(12) United States Patent
Kaufman et al.

(10) Patent No.: US 10,500,385 B2
(45) Date of Patent: Dec. 10, 2019

(54) DISPENSING APPLICATOR FOR FLUIDS

(71) Applicant: BIOMED PACKAGING SYSTEMS INC., Norwalk, CT (US)

(72) Inventors: Jack W. Kaufman, Merrick, NY (US); James Brown, Armonk, NY (US)

(73) Assignee: BIOMED PACKAGING SYSTEMS, INC., Norwalk, CT (US)

( * ) Notice: Subject to any disclaimer, the term of this patent is extended or adjusted under 35 U.S.C. 154(b) by 0 days.

(21) Appl. No.: 15/658,459

(22) Filed: Jul. 25, 2017

(65) Prior Publication Data

US 2017/0319838 A1 Nov. 9, 2017

Related U.S. Application Data

(63) Continuation of application No. 14/556,401, filed on Dec. 1, 2014, now Pat. No. 9,717,892, which is a (Continued)

(51) Int. Cl.
*B43K 5/14* (2006.01)
*A61F 13/40* (2006.01)
(Continued)

(52) U.S. Cl.
CPC ........ *A61M 35/006* (2013.01); *A61M 35/003* (2013.01); *B43M 11/06* (2013.01); *A61M 2210/04* (2013.01)

(58) Field of Classification Search
CPC .............. A61M 35/003; A61M 35/006; A61M 2210/04
(Continued)

(56) References Cited

U.S. PATENT DOCUMENTS

D49,667 S 9/1916 Landline
D50,050 S 12/1916 Landline
(Continued)

FOREIGN PATENT DOCUMENTS

GB 2 185 880 2/1987
WO WO 2004-062709 7/2001
(Continued)

OTHER PUBLICATIONS

International Search Report and Written Opinion, PCT/US2013/057017 dated Nov. 19, 2013, 19 pages.
(Continued)

*Primary Examiner* — Jennifer C Chiang
(74) *Attorney, Agent, or Firm* — Andrew F. Young, Esq.; Lackenbach Siegel, LLP

(57) ABSTRACT

A liquid dispensing applicator may include a liquid source for housing a liquid, the liquid source having a first end and a second end, the second end being closed; a swab member for dispensing said liquid, the swab member being disposed at the first end; and at least one capillary member being in fluid communication with the liquid source, the capillary tube directing fluid out from the liquid source onto an exterior of the swab member upon application of pressure to the liquid source. A liquid dispensing applicator may also include an applicator tip fluidically connected to the liquid source including a frangible juncture and a tongue member coupled to the frangible junction, application of force to the tongue member causing the frangible junction to fracture while remaining attached to the tongue member, resulting in at least one aperture to form through which liquid from the liquid source is dischargeable.

14 Claims, 11 Drawing Sheets

Related U.S. Application Data continuation of application No. 13/971,425, filed on Aug. 20, 2013, now Pat. No. 8,926,211, which is a continuation of application No. 13/485,013, filed on May 31, 2012, now Pat. No. 8,608,397, which is a continuation of application No. 13/102,973, filed on May 6, 2011, now Pat. No. 8,215,859, which is a continuation of application No. 12/579,728, filed on Oct. 15, 2009, now Pat. No. 7,946,779, which is a continuation of application No. 11/138,142, filed on May 26, 2005, now Pat. No. 7,614,811.

(51) Int. Cl.
*A61M 35/00* (2006.01)
*B43M 11/06* (2006.01)

(58) Field of Classification Search
USPC .................................... 401/132–134
See application file for complete search history.

(56) References Cited

U.S. PATENT DOCUMENTS

| | | |
|---|---|---|
| 1,284,635 A | 11/1918 | Ford |
| 2,127,794 A | 8/1938 | Wastman |
| 2,505,295 A | 4/1950 | Meyers |
| D170,451 S | 9/1953 | Drell |
| D193,588 S | 9/1962 | Green |
| 3,063,084 A | 11/1962 | Marinus |
| 3,134,124 A | 5/1964 | Horn |
| D204,831 S | 5/1966 | Goldberg |
| 3,271,810 A | 9/1966 | Raffe |
| 3,285,479 A | 11/1966 | Porter et al. |
| 3,324,855 A | 6/1967 | Heimlich |
| 3,473,681 A | 10/1969 | Samuel, Jr. |
| 3,774,609 A | 11/1973 | Schwartzman |
| 3,777,949 A | 12/1973 | Chiquiari-Arias |
| 3,847,151 A * | 11/1974 | D'Alessandro .......... A47L 17/00 15/244.1 |
| D245,221 S | 8/1977 | Hoyt |
| 4,218,155 A | 8/1980 | Weidner |
| 4,328,907 A | 5/1982 | Beard |
| 4,415,288 A | 11/1983 | Gordon et al. |
| D271,741 S | 12/1983 | Riccio |
| 4,732,287 A | 3/1988 | Bennett |
| 4,747,720 A | 5/1988 | Bellehumeur et al. |
| D296,765 S | 7/1988 | Urion |
| 5,090,832 A | 2/1992 | Rivera et al. |
| 5,098,297 A * | 3/1992 | Chari .................. A61M 35/006 401/132 |
| 5,229,061 A | 7/1993 | Van Dyke et al. |
| 5,302,358 A | 4/1994 | Andersen et al. |
| 5,435,660 A | 7/1995 | Wirt |
| 5,586,672 A | 12/1996 | Schneider et al. |
| 5,658,084 A | 8/1997 | Wirt |
| D419,070 S | 1/2000 | Scheuermann |
| 6,042,286 A | 3/2000 | Pazienza |
| 6,082,919 A | 7/2000 | De Laforcade |
| D447,946 S | 9/2001 | Tsuruishi et al. |
| 6,283,933 B1 * | 9/2001 | D'Alessio .......... A61M 35/003 401/132 |
| 6,299,377 B1 * | 10/2001 | Emerit ................ A61M 35/006 222/541.1 |
| 6,533,484 B1 | 3/2003 | Osei et al. |
| D473,790 S | 4/2003 | Nottingham et al. |
| 6,554,156 B1 | 4/2003 | Chong |
| 6,595,940 B1 * | 7/2003 | D'Alessio .......... A61M 35/003 401/132 |
| D487,398 S | 3/2004 | Bremmer et al. |
| 6,711,879 B2 | 3/2004 | Korteweg et al. |
| 7,063,476 B1 | 6/2006 | Pinnix et al. |
| D546,682 S | 7/2007 | Decottigales et al. |
| 7,614,811 B2 | 11/2009 | Kaufman et al. |
| 7,946,779 B2 | 5/2011 | Kaufman et al. |
| 8,083,425 B2 | 12/2011 | Kaufman et al. |
| 8,186,897 B2 | 5/2012 | Kaufman et al. |
| 8,215,859 B2 | 7/2012 | Kaufman et al. |
| D678,765 S | 3/2013 | Brown |
| D682,100 S | 5/2013 | Brown |
| 8,511,923 B2 | 8/2013 | Kaufman et al. |
| 8,608,397 B2 | 12/2013 | Kaufman et al. |
| 8,628,265 B2 | 1/2014 | Kaufman et al. |
| D718,131 S | 11/2014 | Brown |
| D721,581 S | 1/2015 | Brown |
| 8,926,211 B2 | 1/2015 | Kaufman et al. |
| 9,073,382 B2 | 7/2015 | Kaufman et al. |
| D737,143 S | 8/2015 | Brown |
| 9,220,881 B2 | 12/2015 | Kaufman et al. |
| 2004/0253039 A1 | 12/2004 | Stenton |
| 2006/0269355 A1 | 11/2006 | Kaufman |
| 2007/0205233 A1 | 9/2007 | Petit et al. |
| 2011/0142527 A1 | 6/2011 | Kaufman et al. |

FOREIGN PATENT DOCUMENTS

| | | |
|---|---|---|
| WO | WO 2004-062709 | 7/2004 |
| WO | WO 2006-041801 | 4/2006 |
| WO | WO 2006/041801 | 4/2006 |
| WO | WO 2007/018541 | 2/2007 |

OTHER PUBLICATIONS

PCT/US2008/061776, International Search Report and Written Opinion mailed Oct. 17, 2008. 10 pages.
EP Pat. Appln. No. 08 769 216.6, Supplementary EP Search Report, 10 pages, dated Feb. 17, 2012.
PCT/US2008/061776, European Office Action dated Mar. 7, 2012, received Mar. 13, 2012, 11 pages.
EP Pat. Appln. No. 08 769 216.6, Communication pursuant to Rules 70(2) and 70a(2) EPC, 1 page, dated Mar. 7, 2012.
Internaional Search Report and Written Opinion, PCT/US2013/057017 dated Nov. 19, 2013, 19 pgs.

* cited by examiner

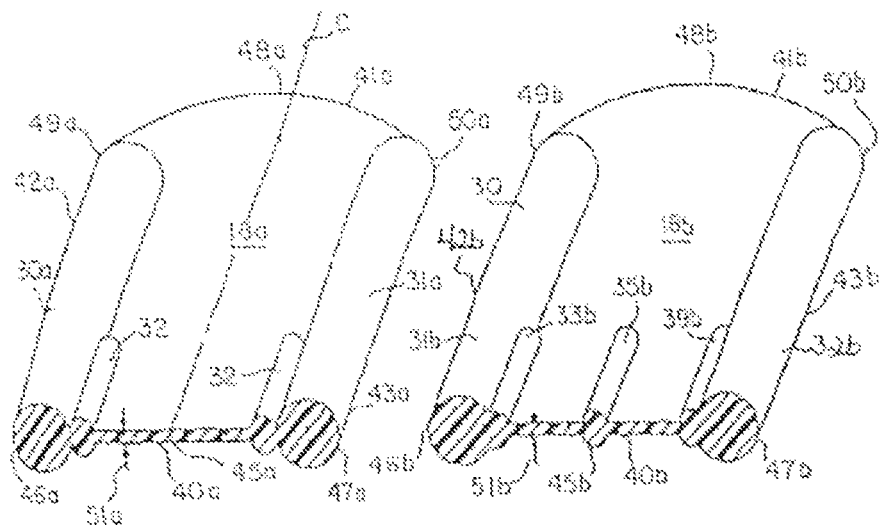
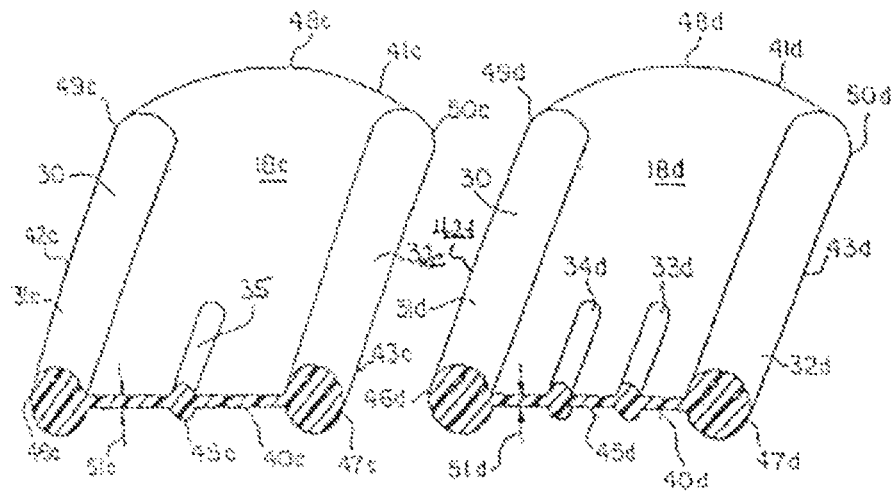

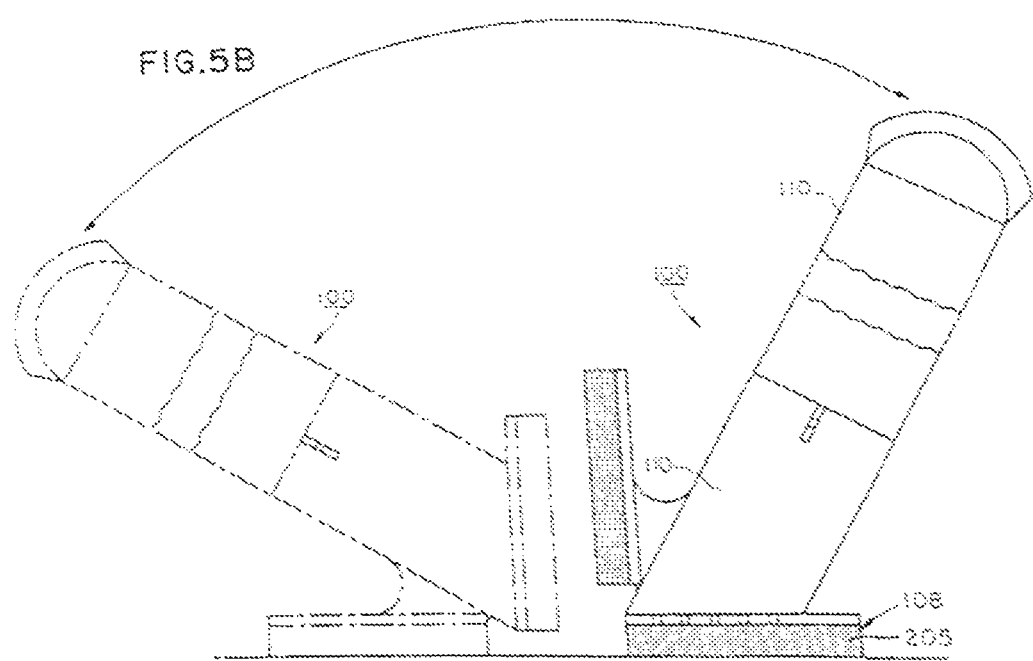

DISPENSING APPLICATOR FOR FLUIDS

CROSS REFERENCE TO RELATED APPLICATIONS

This application is a continuation of, and claims priority from, co-pending U.S. patent application Ser. No. 14/556,401 for a DISPENSING APPLICATOR FOR FLUIDS filed Dec. 1, 2014 (now allowed), which is a continuation of, and claims priority from, U.S. patent application Ser. No. 13/971,425 for a DISPENSING APPLICATOR FOR FLUIDS filed Aug. 20, 2013, now U.S. Pat. No. 8,926,211 issued Jan. 6, 2015, which in turn is a continuation of and claims to priority from, U.S. patent application Ser. No. 13/485,013 for a DISPENSING APPLICATOR FOR FLUIDS, which is now U.S. Pat, No. 8,608,397 issued Dec. 17, 2013, which in turn is a continuation of and claims to priority from, U.S. patent application Ser. No. 13/102,973 for a DISPENSING APPLICATOR FOR FLUIDS, which is now U.S. Pat. No. 8,215,859, which in turn is a continuation of and claims to priority from, U.S. patent application Ser. No. 12/579,728 for a DISPENSING APPLICATOR FOR FLUIDS, which is now U.S. Pat. No. 7,946,779 issued May 24, 2011, which in turn is a continuation of and claims to priority from, U.S. patent application Ser. No. 11/138,142 for a DISPENSING APPLICATOR FOR FLUIDS, now U.S. Pat. No. 7,614811 issued Nov. 10, 2009, and incorporates those applications in their entirety herein by reference.

FIGURE SELECTED FOR PUBLICATION

FIG.11B

BACKGROUND OF THE INVENTION

Field of the Invention

The present invention is directed in general to means for swabbing a surface (i.e., skin) that is gripped by a user at one end and has a sponge or absorbent material at the other end. Further, the present invention is directed to such means for swabbing a surface having a source of a fluid (e.g., disinfectant or medicament) in communication with the sponge or absorbent material. Specifically, the present invention is directed to such a fluid-containing means for swabbing a surface further having means that is fractured or separated for the purpose of allowing the fluid to flow from the fluid source to the sponge or absorbent material.

Description of the Related Art

Applicators consisting of a wooden or plastic tube having a bud of cotton on one or both ends, are widely used for numerous purposes, such as the topical application of substances to the human body. A demand exists for a product of this kind which serves not only as an applicator, but also as a container for substances that are to be applied to the human body. To be practical, such a device would have to have a manually frangible portion that can readily be broken, while at the same time being so constructed so as to prevent inadvertent fracture. An applicator of this nature would be useful for numerous purposes.

Prior dispensing applicators allow excess amount fluid to flow too quickly, and the fluid tends to pool on the surface. Depending upon the fluid being dispensed, such pooling can lead to patient discomfort, chemical burns, and even electrical shock if the dispensed fluid comes into contact with electrical leads attached to the patient's body.

Moreover, in prior art dispensing applicators, the dispensed fluid tends to accumulate at the rear-most portion of the absorbent member, which is closest to the fluid source, instead of preferably evenly spreading throughout the absorbent member, As the volume of the dispensed fluid gradually increases at the rear portion of the absorbent member, the fluid starts uncontrollably dripping, thus, causing substantial inconvenience to a user.

A need, therefore, exists for a dispensing applicator overcoming the above-identified drawbacks of the known related art.

A further need exists for a hand-held dispensing applicator that has a simple structure allowing the practitioner to deliver fluid to the surfaces to be treated in a controllable manner.

Another need exists for a dispensing applicator that has an easily actuatable structure requiring minimal application of manual force.

Further, a need exists for a hand-held dispensing applicator that has a structure minimizing uncontrollable distribution of fluid.

ASPECTS AND SUMMARY OF THE INVENTION

The present invention relates to a liquid dispensing applicator. The applicator may include a liquid source for housing a liquid, the liquid source having a first end and a second end, the second end being closed; a swab member for dispensing said liquid, the swab member being disposed at the first end; and at least one capillary member being in fluid communication with the liquid source, the capillary tube directing fluid out from the liquid source onto an exterior of the swab member upon application of pressure to the liquid source. The at least one capillary member may include a capillary tube, the capillary tube traversing the absorbent member. The swab member may include an inner surface in fluid communication with the fluid source. The applicator may further include an absorbent member, the absorbent member adjacent to the swab member, which may be configured to not be in fluid communication with the liquid source. The absorbent member and the swab member may have center axes extending through exterior surfaces thereof, the center axes being orthogonal with respect to one another. The liquid source has an axis extending lengthwise through the liquid source, the axis extending lengthwise through the liquid source being disposed substantially between the swab and absorbent members. The at least one capillary member may include a capillary vessel disposed between the swab member and the liquid source, the capillary vessel permitting flow of fluid from the fluid source to the swab member only upon application of a predetermined amount of pressure to the fluid source. An attachment member may be coupled to the fluid source, the capillary vessel traversing through the attachment member. The attachment member may be configured to direct liquid from the fluid source toward a center axis extending lengthwise through the fluid source. An applicator tip may be disposed at a distal end of the attachment member, the applicator tip comprising a frangible portion and a tongue member.

A liquid dispensing applicator may include a liquid source for housing a liquid, the liquid source having a first end and a second end, the second end being closed; and an applicator tip fluidically connected to the liquid source, the applicator tip including a frangible juncture and a tongue member coupled to the frangible junction, application of force to the tongue member causing the frangible junction to fracture while remaining attached to the tongue member, resulting in at least one aperture to form through which liquid from the liquid source is dischargeable. The tongue member may include at least one reinforcing rib connected to frangible juncture. The at least one reinforcing tip may be configured to inhibit flexing of the tongue member and to concentrate the applied force at the frangible juncture. The at least one reinforcing rib may include a first rib at a first end of the frangible juncture and a second rib at a second end of the frangible juncture and a third rib therebetween, the first and second ribs being configured to break while the third rib remains secured to the frangible juncture. The tongue member may be hingedly connected to the frangible juncture, flexing of the tongue member relative to the frangible juncture causing the frangible juncture to fracture. The applicator tip may be disposed within an absorbent applicator member, The absorbent applicator member may be multi-sided.

The above and other aspects, features and advantages of the present invention will become apparent from the following description read in conjunction with the accompanying drawings, in which like reference numerals designate the same elements.

BRIEF DESCRIPTION OF THE DRAWINGS

A further understanding of the present invention can be obtained by reference to a preferred embodiment set forth in the illustrations of the accompanying drawings. Although the illustrated preferred embodiment is merely exemplary of methods, structures and compositions for carrying out the present invention, both the organization and method of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which:

FIG. 4A is a perspective view of a first preferred tongue member for an applicator tip for the dispensing applicator of FIG. 1;

FIG. 4B is a perspective view of a second preferred tongue member for an applicator tip for the dispensing applicator of FIG. 1;

FIG. 4C is a perspective view of a third preferred tongue member for an applicator tip for the dispensing applicator of FIG. 1;

FIG. 4D is a perspective view of a fourth preferred tongue member for an applicator tip for the dispensing applicator of FIG. 1;

FIG. 5B is a diagrammatic view illustrating two positions of the dispensing applicator of FIG. 5;

DETAILED DESCRIPTION OF THE PREFERRED EMBODIMENTS

Figure 1:
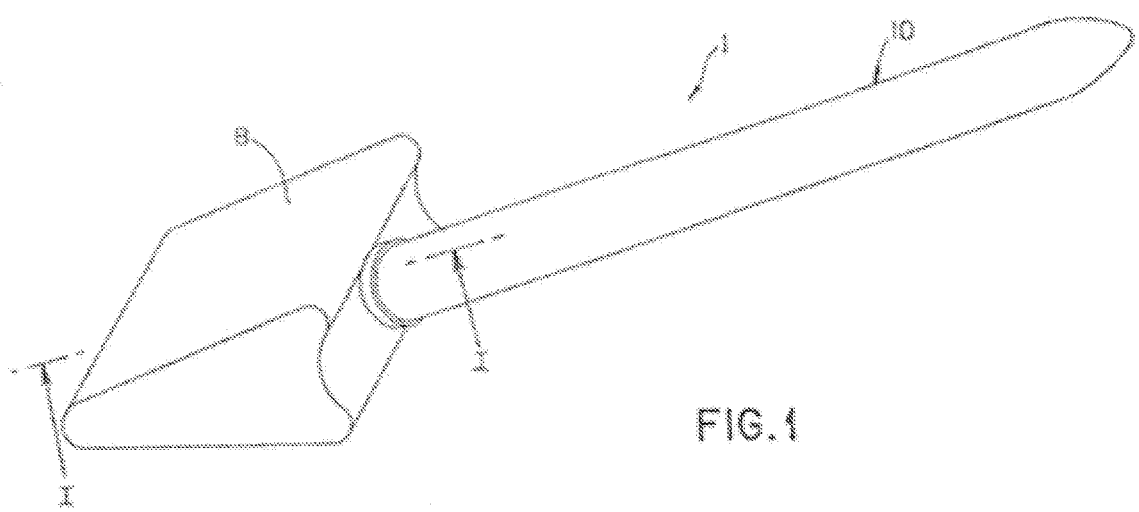
FIG. 1 is a side elevational view of a dispensing applicator according to the present invention.

As required, a detailed illustrative embodiment of the present invention is disclosed herein. However, techniques, systems, compositions and operating structures in accordance with the present invention may be embodied in a wide variety of sizes, shapes, forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention.

Reference will now be made in detail to several embodiments of the invention that are illustrated in the accompanying drawings. Wherever possible, same or similar reference numerals are used in the drawings and the description to refer to the same or like parts or steps. The drawings are in simplified, form and are not to precise scale. For purposes of convenience and clarity only, directional terms, such as top, bottom, up, down, over, above, below, etc., or motional terms, such as forward, back, sideways, transverse, etc. may be used with respect to the drawings. These and similar directional terms should not be construed to limit the scope of the invention in any manner.

Figure 2:
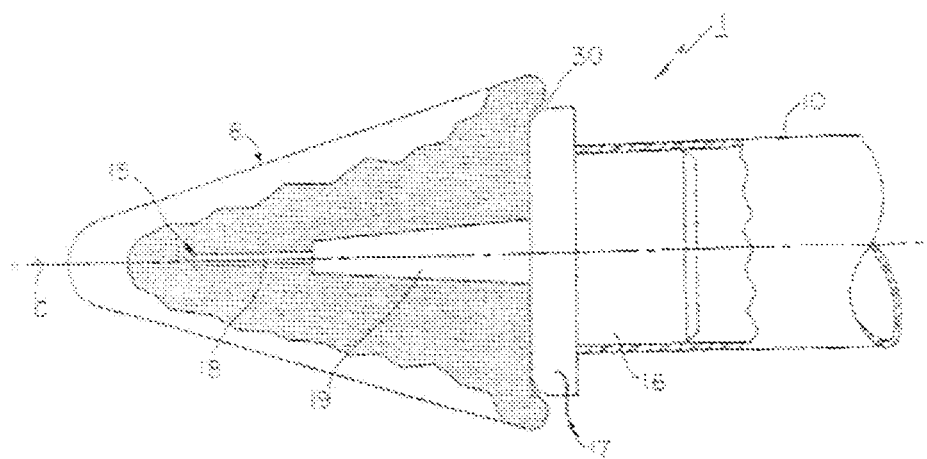
FIG. 2 is a side cross-sectional view of the dispensing applicator of FIG. 1.

Referring to the drawings, FIGS. 1 and 2 in particular, illustrate a dispensing applicator according to the present invention generally indicated as reference numeral 1. Dispensing applicator 1 comprises an absorbent applicator member 8, a fluid source 10, and an applicator tip 15. Absorbent member 8 may be of any suitable shape, such as cubic, cylindrical, or conical, and comprise any suitable absorbent material, such as cotton or sponge. Fluid source 10 may have any suitable shape. As is shown in FIG. 1, fluid source 10 is preferably a hollow, generally cylindrical body. The end of fluid source body located adjacent to absorbent member 8 is preferably sealed thereto at a joint or seam 30, such as by heat sealing, to enclose the fluid substance contained within fluid source body 10. Applicator tip 15 comprises an attachment member 16, an attachment portion 17, and tongue member 18 joined thereto by a tapered frangible region or juncture 19. Tongue member 18 is preferably a flat and broad shape that extends a distance into absorbent member 8, such that tongue member 18 is longer than it is wide (see FIGS. 4A to 4D). It should be noted that, the attachment portion 17 is relatively thick adjacent the fluid source body 10, and tapers toward frangible juncture 19. Absorbent member 8 is preferably connected to attachment portion 17 and/or fluid source body 10.

The manner of utilizing dispensing applicator 1 will be self-evident, and simply involves holding the dispensing applicator 1 with the absorbent application member 8 against an application surface. Dispensing applicator 1 is held such that tongue member 18 is at an acute angle (i.e., substantially parallel) to the application surface. Sufficient downward pressure of tongue member 18 against the application surface will deflect tongue member 18 from the central, axis c of the fluid source body 10. At a predetermined amount of deflection, the frangible juncture 19 will fracture or break. Fracture of the frangible juncture 19 will desirably be achieved by the application of approximately 0.25 to 5 pounds of force of tongue member 18 against the application surface.

Figure 3C:
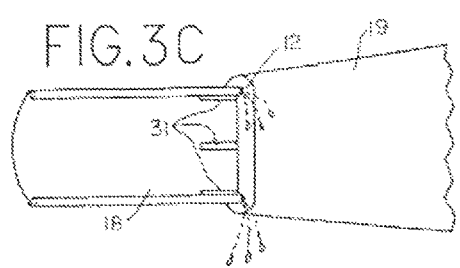
FIG. 3C is a top view of the applicator tip of FIG. 3B wherein apertures are formed in the broken frangible region.
Figure 3B:
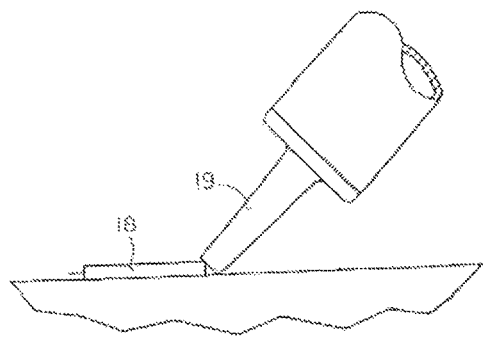
FIG. 3B is a side elevational view of the applicator tip of FIG. 3 wherein the frangible region is broken.

As shown in FIGS. 3B and 3C, breaking frangible juncture 19 will result in the formation of one or more apertures 12 through which fluid from source body 10 may flow into absorbent member 8 (not shown).

In its most preferable form, all portions of the source body 10 will have a wall thickness that is substantially uniform at a value of about 0.005 inch to about 0.025 inch (about 0.127 mm to about 0.635 mm). The source body 10 is preferably made of polypropylene having a density of 0.897 g/cm$^2$ and a flexural modulus of about 150 Kpsi (about 1035 MPa), as determined by ASTM method 790B. The source body 10 is preferably about 6 inches to about 10 inches in overall length, and about 0.25 to about 1.0 inches in diameter, so as to be convenient to grasp and still contain sufficient fluid for a single application.

The applicator tip 15 is about 1 to 3 inches long, and about 0.325 inches in diameter. The frangible juncture 19 will preferably have a thickness of about 0.0005 inch to about 0.002 inch (about 0.013 mm to about 0.050 mm). The one or more apertures 12, which are produced by the fracture of frangible juncture 19, may be of any suitable size, but preferably have a width and height that is substantially correlated to the width and thickness of large ribs 31, 32 (see FIG. 3).

Figure 3A:
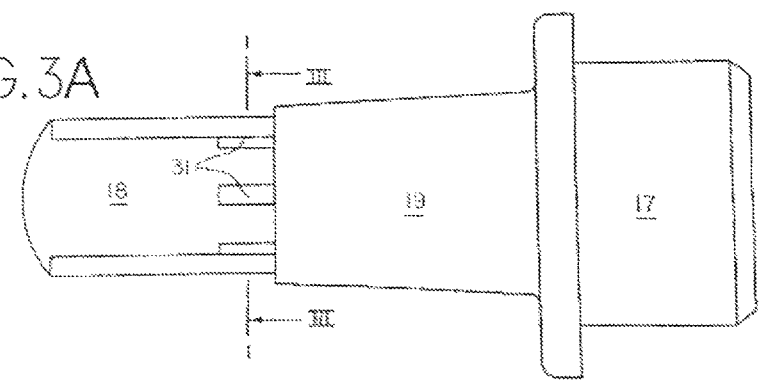
FIG. 3A is a front devotional view of a preferred applicator tip for the dispensing applicator of FIG. 1.

Referring to FIGS. 3A and 3C, tongue member 18 preferably comprises a plurality of reinforcing ribs 31, 32. Due to the reinforcing ribs and the resultant rigidity of tongue member 18, there will be virtually no flex along the length of tongue 18, and an applied force on tongue member 18 will be effectively entirely transferred to and concentrated at frangible juncture 19. The result will be the reliable fracturing of frangible juncture 19, which fracturing results in the formation of one or more apertures 12 of suitable size to permit the fluid within the fluid source body 10 to be discharged therefrom and distributed across a predetermined area of absorbent application member 8 (FIG. 1). As noted above, it will generally be desirable for the material forming fluid source body 10 to be sufficiently thin to permit some compression of fluid source body 10, so as to enable discharge of a liquid therein at a faster rate than would otherwise occur, and/or to promote the flow of the fluid, especially if the fluid is relatively viscous.

FIG. 4A illustrates a first arrangement of ribs for a tongue 18a. As shown, tongue 18a is rectilinear in shape with a bottom edge 40a, a top edge 41a, and side edges 42a, 43a. Bottom edge 40a is substantially linear with a central point 45a and corners 46a, 47a at which the proximate ends of respective side edges 42a, 43a meet. Top edge 41a is curvilinear with an apex 48a and corners 49a, 50a at which the distal ends of respective side edges 42a, 43a terminate. Central point 45a and apex 48a lie along central axis c. The distance between central point 45a and apex 48a is the length of tongue 18a, while the distance between corners 49a, 50a is the width of tongue 18a. The thickness 51a of tongue 18a is the distance between the top and bottom surfaces thereof. Side edges 42a, 43a each have a respective large rib 31a, 30a extending along the entire length thereof. It is notable that tongue 18a extends a distance beyond the length of the large ribs 31a, 30a, to apex 48a, whereby top edge 41a is not reinforced. Ribs 31a, 30a are each about 3 times the thickness of tongue 18a and about $\frac{1}{5}^{th}$ the width of tongue 18a. Small ribs 32 are disposed directly adjacent to their respective large rib 31a, 30a on the side thereof that is proximate to central axis c. Each small rib 32 extends from bottom edge 40a for a distance that is about $\frac{3}{10}^{th}$ the length of the large ribs 31a, 32a. Each small rib 32 is about 2 times the thickness of tongue 18a and about $\frac{1}{10}^{th}$ the width of tongue 18a.

FIG. 4B illustrates a second arrangement of ribs for a tongue 18b. As shown, tongue 18b is rectilinear in shape with a bottom edge 40b, a top edge 41b, and side edges 42b, 43b. Bottom edge 40b is substantially linear with a central point 45b and corners 46b, 47b at which the proximate ends of respective side edge 42b, 43b meet. Top edge 41b is curvilinear with an apex 48b and corners 49b, 50b at which the distal ends of respective side edges 42b, 43b terminate. Central point 45b and apex 48b lie along central axis c (see FIG. 2). The distance between central point 45b and apex 48b is the length of tongue 18b, while the distance between corners 49b, 50b is the width of tongue 18b. The thickness 51b of tongue 18b is the distance between the top and bottom surfaces thereof. Side edges 42b, 43b each have a respective large rib 31b, 32b extending along the entire length thereof. Large ribs 31b are each about 3 times the thickness of tongue 18b and about $\frac{1}{5}^{th}$ the width of tongue 18b. Small half-ribs 33b, 34b are disposed directly adjacent to their respective large ribs 31b on the sides thereof that are proximate to central axis c. A small rib 35b is disposed along central axis c. Each small half-rib 33b, 34b extends from bottom edge 40b a distance that is about $\frac{3}{10}^{th}$ the length of the large ribs 31b. Each small half-rib 33b, 34b is about 2 times the thickness of tongue 18b and about $\frac{1}{20}^{th}$ the width of tongue 18b. The small rib 35b is about 2 times the thickness of tongue 18b and about $\frac{1}{10}^{th}$ the width of tongue 18b.

FIG. 4C illustrates a third arrangement of ribs for a tongue 18c. As shown, tongue 18c is rectilinear in shape with a bottom edge 40c, a top edge 41c, and side edges 42c, 43c. Bottom edge 40c is substantially linear with a central point 45c and corners 46c, 47c at which the proximate ends of respective side edge 42c, 43c meet. Top edge 41c is curvilinear with an apex 48c and corners 49c, 50c at which the distal ends of respect side edges 42c, 43c terminate. Central point 45c and apex 48c lie along central axis c (see FIG. 2), The distance between central point 45c and apex 48c is the length of tongue 18c, while the distance between corners 49c, 50c is the width of tongue 18c. The thickness 51c of tongue 18c is the distance between the top and bottom surfaces thereof. Side edges 42c, 43c each has a respective large rib 31c, 32c extending along the entire length thereof. Large ribs 31c, 32c are each about 3 times the thickness of tongue 18c and about $\frac{1}{5}^{th}$ the width of tongue 18c. A small rib 35c is disposed along central axis c. The small rib 35c extends from bottom edge 40c a distance that is about ³/₁₀ the length of the large ribs 31. The small rib 35c is about 2 times the thickness of tongue 18c and about $1/10^{th}$ the width of tongue 18c.

FIG. 4D illustrates a fourth arrangement of ribs for a tongue 18d. As shown, tongue 18d is rectilinear in shape with a bottom edge 40d, a top edge 41d, and side edges 42d, 43d. Bottom edge 40d is substantially linear with a central point 45d and corners 46d, 47d at which the proximate ends of respective side edge 42d, 43d meet. Top edge 41d is curvilinear with an apex 48d and corners 49d, 50d at which the distal ends of respect side edges 42d, 43d terminate. Central point 45d and apex 48d both lie along central axis c (see FIG. 2). The distance between central point 45d and apex 48d is the length of tongue 18d, while the distance between corners 49d, 50d is the width of tongue 18d. The thickness 51d of tongue 18d is the distance between the top and bottom surfaces thereof. Side edges 42d, 43d each has a respective large rib 31d, 32d extending along the entire length thereof. Large ribs 31d, 32d are each about 3 times the thickness of tongue 18d and about $1/5^{th}$ the width of tongue 18d. Spaced apart from each large rib 31d, 32d is a respective small rib 33d, 34d. The small ribs 33d, 34d are spaced apart from each other and evenly spaced from central axis c. The small ribs 33d, 34d are closer to central axis c than to their respective large ribs 31d, 32d. The small ribs 33d, 34d extend from bottom edge 40b a distance that is about ³/₁₀ the length of the large ribs 31d, 32d. The small ribs 33d, 34d are about 2 times the thickness of tongue 18b and about $1/10^{th}$ the width of tongue 18b. Each small rib 33d, 34d is spaced apart from the central axis c by a distance that is approximately equal to its respective width. The small ribs 33d, 34d are spaced apart from each other by a distance that is approximately equal to 2 times the width of either small rib 33d or 34d. Each small rib 33d, 34d is spaced apart from its respective large rib 31d, 32d by a distance that is approximately equal to 2 times its respective width.

Figure 5A:
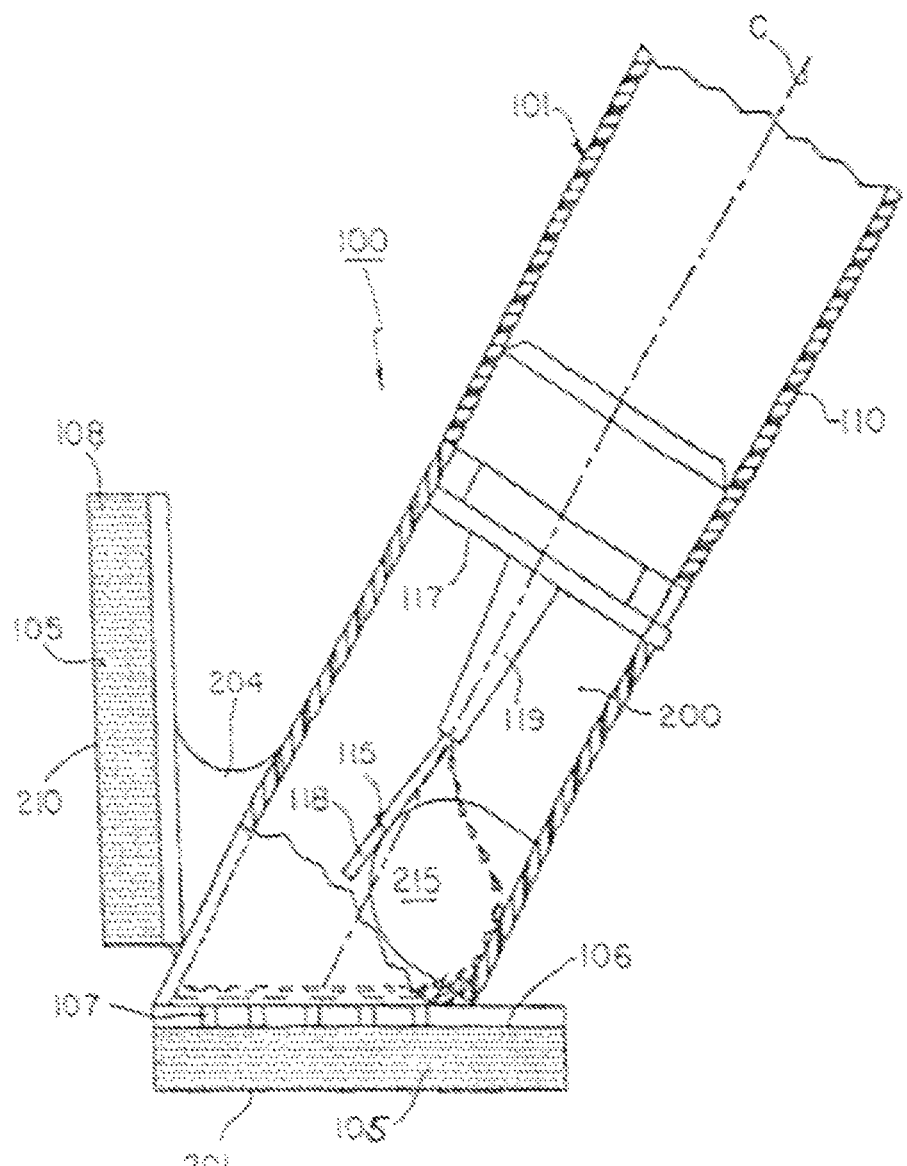
FIG. 5A is a cross-sectional side view of the dispensing applicator constructed in accordance with a further embodiment of the invention.

FIGS. 5A and 5B illustrate a second dispensing applicator 100 according to the present invention. Dispensing applicator 100 comprises an applicator head 108, a source of fluid, which is shown as a hollow, generally cylindrical body 110, and an applicator tip 115, which has an attachment member 117 and tongue member 118 joined thereto by a tapered frangible juncture 119. Fluid source body 110 and applicator tip 115 are respectively identical in form and function to fluid source body 10 and applicator tip 15 described hereinabove in reference to FIGS. 1 through 4D.

In addition, dispensing applicator member 100 is provided with an absorbent swab member 210, and an inwardly projecting ridge-shaped member 215 provided within body 110. A portion of body 110 is adapted to hold and/or support absorbent applicator member 105. As shown, absorbent applicator member 105 is held and supported on a surface 106. Surface 106 is provided with at least one aperture 107, such that the fluid may flow from the interior of body 110 into absorbent applicator member 105, as discussed in further detail herein below. Furthermore, a portion of body 110 is adapted to hold and/or support absorbent swab member 210.

As shown, absorbent swab member 210 is held and supported on a surface 101 that is connected to body 110 by a stock member 204. Absorbent swab member 210 is preferably not in fluid communication with the interior of body 110. Outer surface 201 of applicator member 105 is oriented relative to body 200 such that, when absorbent applicator member 105 is substantially parallel to an application surface (i.e., in contact with the application surface), the central axis c of body 110 forms an angle of about 45° with the application surface, which angle provides a comfortable grip for the user and facilitates the flow of fluid through the interior of body 110 into absorbent application member 105. Similarly, outer surface 201 of swab member 210 is oriented relative to body 200, such that, when absorbent swab member 210 is substantially parallel to an application surface (i.e., in contact with the application surface), the central axis c of body 200 forms an angle of about 30° with the application surface, which angle provides a comfortable grip for the user and allows the user to spread the applied fluid over a relatively large area with relatively less arm movement and/or extension.

The manner of utilizing dispensing applicator 100 involves holding the dispensing applicator 100 with the absorbent application member 105 against an application surface. Downward pressure of applicator 100 against the application surface will displace head 108 upwardly and force ridge-shaped member 215 into contact with tongue member 118. Sufficient upward pressure of ridge-shaped member 215 against tongue member 118 will upwardly deflect the tongue member 118 from the central axis c of the fluid source body 110. At a predetermined amount of deflection, the frangible juncture 119 will fracture or break. Fracture of the frangible juncture 119 will desirably be achieved by the application of approximately 0.25 to 5 pounds of downward force of applicator 100 against the application surface. Breaking frangible juncture 119 will result fluid from fluid source body 110 flowing into head 108. Comparable to breaking frangible region 19 of applicator tip 15, as discussed hereinabove reference to FIGS. 3A to 3C, breaking frangible region 119 of applicator tip 115 results in the formation of one or more apertures in applicator tip 115 through, which fluid from source body 110 may flow into head 108. Thus, in general, applicator tip 15 is comparable in form and structure to applicator tip 115.

Absorbent swab member 210 may be employed for a variety of purposes. Swab 210 may be used to spread a fluid over the application surface after the application member 205 initially applies the fluid. Using swab 210 in this way would be particularly advantageous if the amount of fluid that is desired to cover a relatively large surface area has been inadvertently applied to a relatively small area, which may occur if application member 105 becomes over-saturated with fluid and can no longer effectively regulate the flow rate and amount of fluid being applied. Moreover, swab member 210 may be used to soak up fluid on the application surface, for example, when an excess of fluid has been applied or the fluid has been applied over the wrong area.

As stated above, absorbent swab member 210 is preferably not in fluid communication with the interior of body 200. However, a possible use for swab 210 is applying fluid to a second surface area that is separate and apart from the surface area over which used absorbent application member 205. In the critical interest of avoiding cross-contamination, it is desirable to use the application member 105 over only a single contiguous surface area that should be relatively limited (e.g., the upper front of the torso, instead of the entire front of the torso). Accordingly, after an initial application, any additional fluid in a given dispensing applicator may go wastefully unutilized. Therefore, in another embodiment of absorbent applicator head 108, there is provided at least one aperture (not shown) in surface 101, such that fluid may flow from the interior of body 200 into absorbent swab member 210.

Head 108 may be detachable from fluid body 110. Fluid body 110 may contain an amount of fluid that is greater than is necessary for a given application. Accordingly, after an initial application, any additional fluid in a given dispensing applicator may go wastefully unutilized. Therefore, in another embodiment of applicator 100, fluid body 110 is removably attached to head 108 so that head 108 may be disposed of separately from fluid body 110. If fluid body 110 contains residual fluid after an initial application, other absorbent head may be attached to fluid body 110, thereby allowing the residual fluid to be applied to another application surface.

Figure 6:
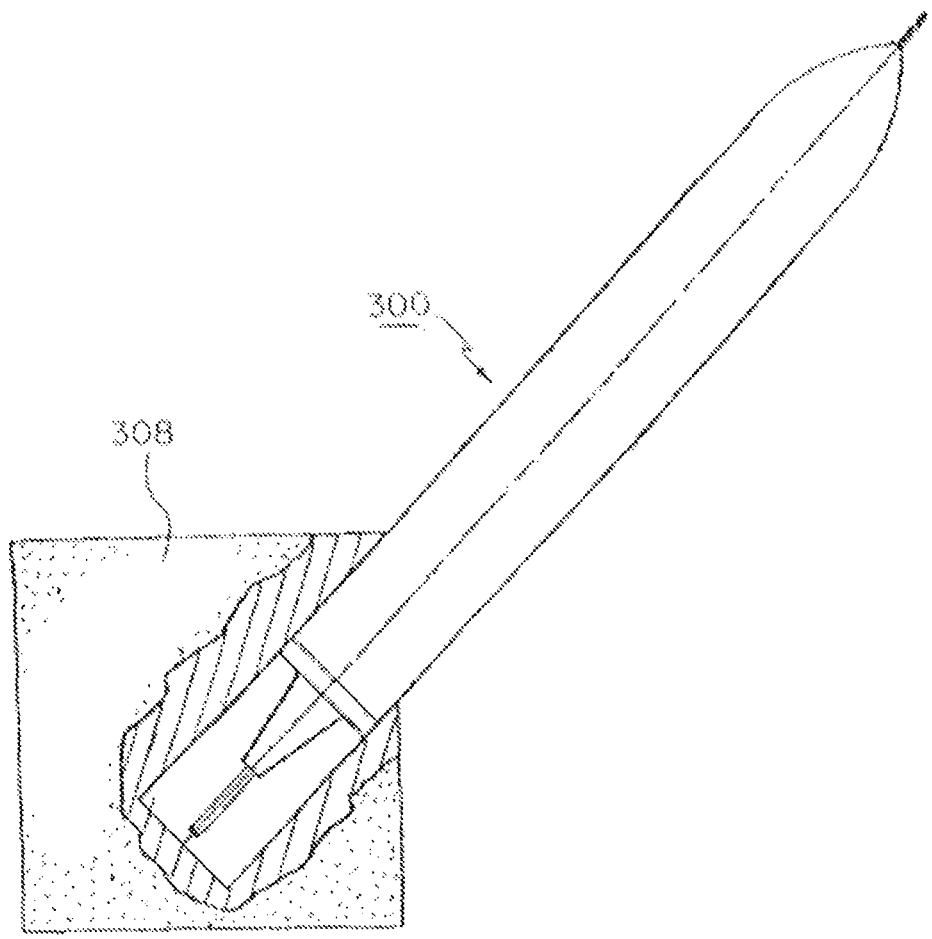
FIG. 6 is a side view of a dispensing applicator structured in accordance with a further embodiment of the present invention and showing a cross-sectional side view of the applicator tip.

Referring to FIG. 6, as stated above, it is desirous to avoid cross-contamination by using a given absorbent applicator over only a single contiguous, relatively limited, surface area. Yet, using a given absorbent application in such a manner will often result in an amount of fluid therein being wasted. Accordingly, a dispensing applicator according to the present invention, generally indicated as reference numeral 300, may be provided with a relatively larger, multi-sided absorbent applicator member 308, such that different sides thereof may be used on different surface areas.

Figure 7:
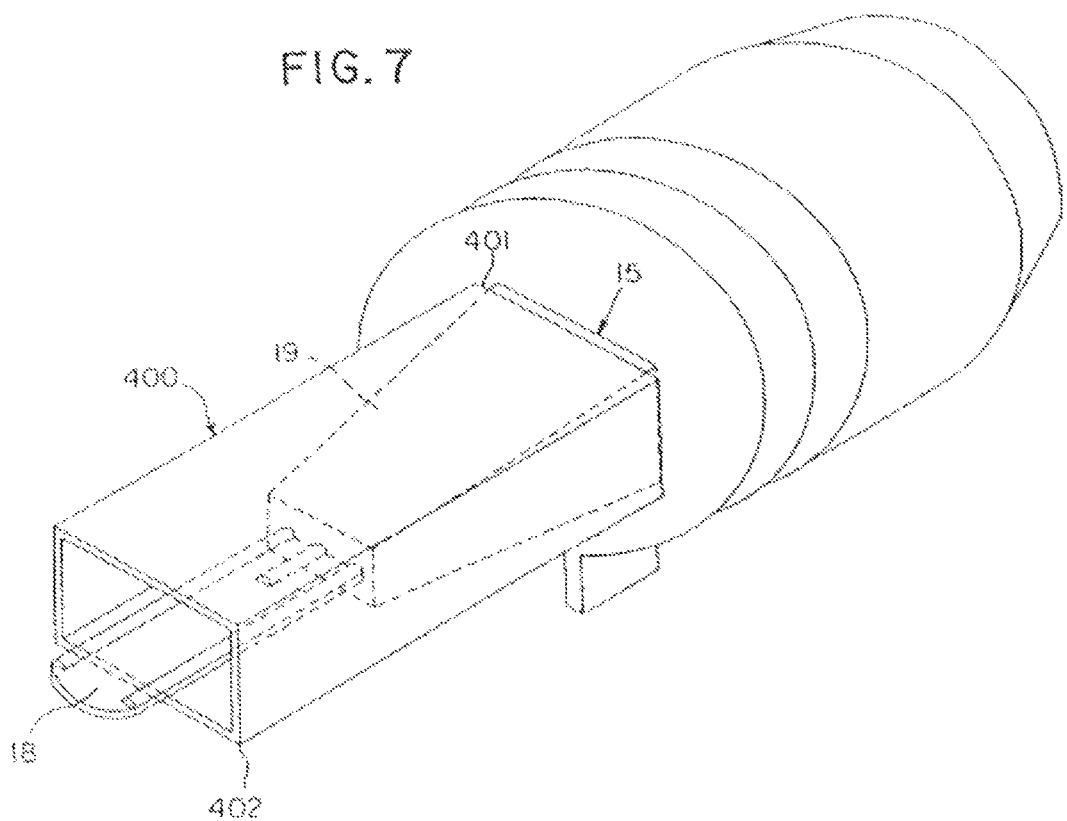
FIG. 7 is a perspective detail view of an applicator tip for use in a dispensing applicator according to the present invention having a semi-cover surrounding the frangible portion to control the speed and direction of the dispersion of the fluid in the absorbent member.

Referring to FIG. 7, there is shown an applicator tip having a semi-permeable or non-permeable cover or shield 400 substantially surrounding frangible juncture 19. The purpose of cover 400 is to control the speed and direction of the dispersion of fluid in a surrounding absorbent member (not shown).

Preferably, a rearward edge 401 of cover 400 will be attached to applicator tip 15. More preferably, rearward edge 401 will be fully sealed around applicator tip 15 without gaps or holes so that fluid may not flow rearward under edge 401. If cover 400 is semi-permeable adjacent to rearward edge 401, fluid may flow rearward through cover 400, but preferably will not flow rearward under edge 401 given the more preferable fully sealed attachment thereof to applicator tip 15. In contrast, a forward or distal edge 402 of cover 400 is preferably free and unattached to applicator tip 15 so that fluid may flow forward under cover 400 substantially without being impeded thereby.

Preferably, cover 400 is formed as a seamless, unitary cylindrical sleeve. Nonetheless, cover 400 may be of any suitable shape and construction. Depending upon its intended function, cover 400 may be semi-permeable or impermeable to fluid. Cover 400 may be made of various materials, including natural and/or synthetic rubbers, thermoplastics (e.g., polyethylene), cellulosic materials or similar fibers (i.e., natural polymeric fibers), and metallic materials. Cover 400 may be a contiguous sheet, a mesh, a felt, or another suitable form, with or without reinforcing fibers and/or seams (i.e., "rip-stop" seams).

Preferably, cover 400 is pliable and flexible so that it does not impede deflection of tongue member 18, In other words, it is preferable that cover 400 does not hinder the breaking of frangible juncture 19.

However, surrounding frangible juncture 19 with a cover 400 having suitable thickness and/or stiffness will provide a level of reinforcement that prevents inadvertent breaking of frangible juncture 19. According, by employing a suitable thick and/or stiff cover 400, tongue member 18 may be provided without reinforcing ribs. Thus, employing cover 400 to reinforce frangible juncture 19 will advantageously simplify production of application tip 15, since tongue member 18 may be molded as a simple flat extension.

Referring again to FIG. 1, a dip mold process may be used to make source body 10, applicator tip 15, or both. The dip molding process begins with preheating of a male mold made from a material having relatively high heat capacity and coefficient of thermal conductivity. This heated mold is then placed in a fluidized bed of meltable particulate resinous material for a time needed to provide a coating of a desired thickness. The mold with melted resinous material is then removed from the fluidized bed, heated a second time and cooled. Finally the tube component is stripped from the mold.

As noted above, it is important for the proper functioning of the applicator that the tube be fabricated from a material that is sufficiently rigid to enable manual fracture of the frangible end portion, If the material is too flexible, deflection of the stem will not produce the desired result. On the other hand, if the material is excessively rigid and brittle, the possibility of an inadvertent fracture will exist, and compression of the body portion to promote flow would be precluded due to the likelihood of cracking, or simply because excess force is required. A variety of synthetic resinous materials may be utilized, the selection of which will be evident to those skilled in the art. The resin must have a sufficiently low melt viscosity to permit coverage of all mold surfaces, and it must produce a nonporous and pinhole-free structure. The polymer will normally be a thermoplastic, and exemplary materials include polypropylene, high density polyethylene, rigid polyvinyl chloride and nylon.

The tongue member of the applicator tip will preferably be elongated to facilitate attachment thereof to the absorbent member 8. However, it is not, essential that the tongue member 18 be of any specific shape and, for example, may be rectangular or cylindrical. Regardless of the shape of tongue member 18, it is essential that suitable reinforcing ribs, as described hereinabove, be included to prevent unintentional breaking of frangible portion 19. Moreover, the shape of tongue member 18 will dictate the shape of the orifice formed in applicator tip 15 where the tongue member 18 is separated from attachment member 17. Accordingly, the flow rate and overall amount of fluid applied to an application surface by dispensing applicator 1 is a function of several factors, including the shape and strength of tongue member 18 (and the resulting orifice), the porosity of absorbent member 8, the density of the fluid, and the force employed by the user when breaking frangible portion 19 and pressing absorbent member 8 against the application surface. Determining the optimal flow rate for a given application is well within the ability of one skilled in the art and, therefore, will not be elaborated upon herein.

As stated above, the porous member may be made of any suitable material(s), most notably open cell, soft, and pliant sponge-like foam, that may be, for example, a polyurethane composition. The choice of material will depend largely upon the particular application and the characteristics of tongue member 18 and the fluid held in source body 10.

In its normal form, source body 10 will be of circular cross-section. However, other shapes are also believed to be feasible. The source body 10 may have a square, triangular, or rectangular cross-section, and the shape may indeed be asymmetrical in cross section and of dissimilar shapes at different points along its length. It will be appreciated therefore that, as used herein the term "diameter" is to be construed in a broad sense, so as to be applicable to non-circular elements corresponding to those shown, and to refer to the maximum cross-sectional dimension of the element. Although normally completely hollow, the source body 10 may include appropriate reinforcement elements, such as internal support pillars, to provide adequate overall strength and rigidity, while permitting the source body 10 to have a thinner than would otherwise be possible. Likewise, source body 10 may include a solid portion, for example, to be gripped while breaking frangible portion 19, so that source body 10 will not be prematurely compressed or squeezed, which might result in too much fluid flowing too quickly into absorbent member 8.

Figure 8:
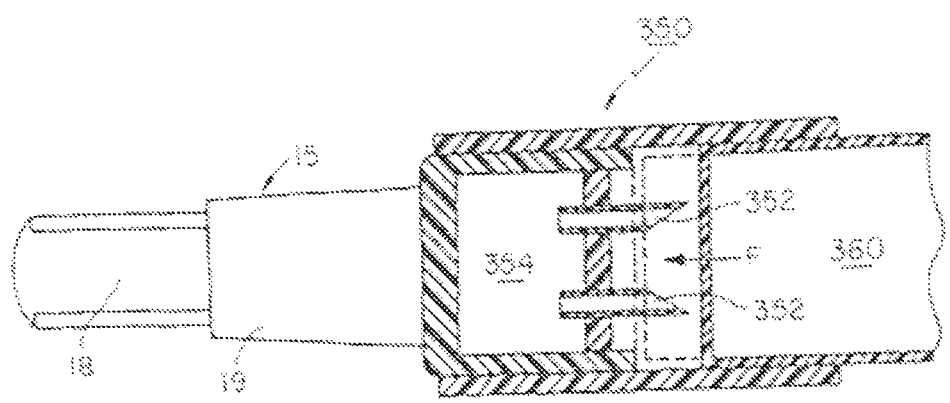
FIG. 8 is a side cross-sectional view of a further aspect of an embodiment of an applicator according to the present invention.

Controlling a rate of dispensing fluid is critical because a) oversaturation of the absorbent member reduces the collecting capability of this member, and b) back flow of the delivered fluid from the distal end towards the proximal end of the absorbent member interferes with the physician's work. Accordingly, FIG. 8 illustrates a further embodiment of the invention directed to a dispensing applicator 350 which is configured to prevent fluid from uncontrollably entering an attachment member 354 that is coupled to tip 15. At least one, but preferably a multiplicity of capillary vessels 352 is provided within the attachment member. Being in fluid communication with a source body 360, vessels 352, by virtue of their cross-section, meter an amount of fluid penetrating into the absorbent member (not shown). Thus, a combination of the openings, which are formed as a result of breaking frangible region 19 and vessels 352, effectively limits oversaturation of the absorbent member.

Figure 9:
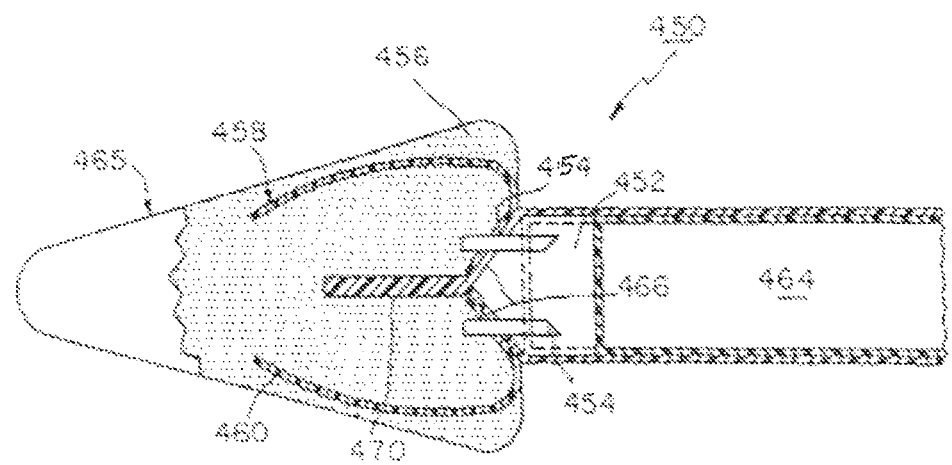
FIG. 9 is a side cross-sectional view of another aspect of an embodiment of the dispensing applicator configured with a collecting and guiding means for minimizing unintended evacuation of fluid via a proximal end of a fluid absorbent member enabling a preferred directional fluid flow.

Still another embodiment of a dispensing applicator 450 is illustrated in FIG. 9. As shown, applicator 450 does not have a frangible structure or region. Instead, an attachment member 452 is provided with at least one or more capillary vessels 454 controllably traverse by fluid from fluid source 464. Vessels 454 project into an applicator tip 465 while penetrating a proximal end of an absorbent, member 456. The cross-section of the vessels is selected to provide a metered delivery of fluid.

However, absorbent member 456 can still accumulate an excessive amount of fluid, which will eventually result in a backflow towards the proximal end of the absorbent member and subsequent voluntary evacuation of fluid via this end. To limit or minimize such a possibility, applicator 450 has a flow limiting component or cover or shield 458. Formed within absorbent member 456 and, preferably, sealed to the proximal end thereof, cover 458 is able to collect fluid flowing towards the proximal end of absorbent member 456 and, thus, prevents uncontrollable evacuation of accumulated fluid.

As illustrated, cover 458 is provided with a body having a pair of concave sides 460 whose free or distal ends are spaced from one another at a distance that defines an open exit/entrance for fluid. The bottom portions 464 of cover 458 extend complementary to converging flanks 466 of attachment member 452. Stability of an applicator tip 465 is added by providing the distal end of attachment member 452 with a rib 470. Note that cover 458 does not completely prevent backflow of fluid leaving a space within the absorbent member which is sufficient to amply, but not excessively, wet the surfaces of this member.

Figure 10A:
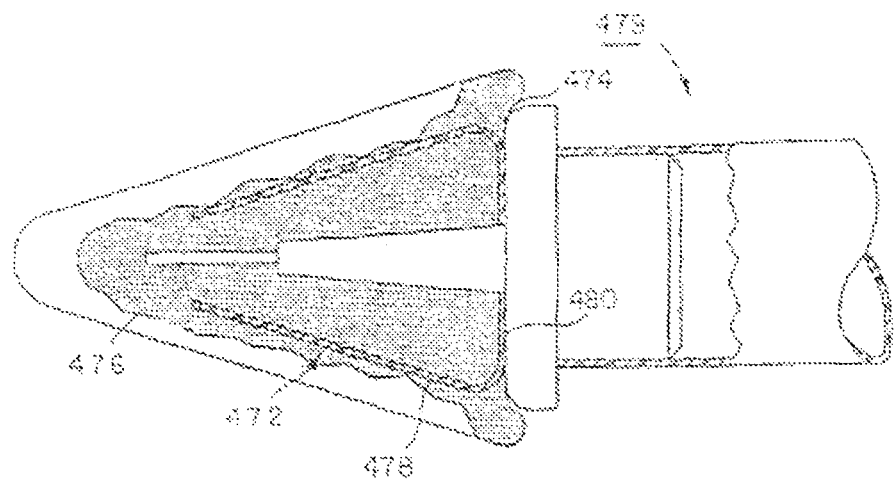
FIG. 10A and 10B are side sectional and rear sectional views of still another embodiment of the present invention.
Figure 10B:
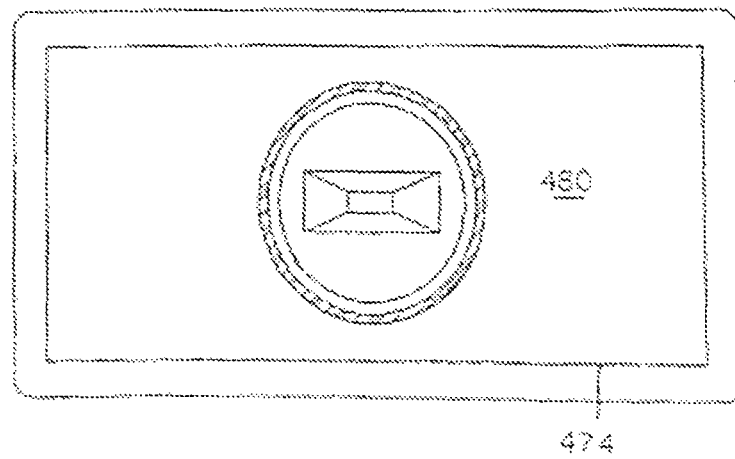

A further embodiment of dispensing applicator 479 is illustrated in FIGS. 10A and 10B. Applicator 479 has a frangible region 19 structured substantially similar to the like configured regions which, are discussed in detail above. To prevent uncontrollable evacuation of fluid via a proximal end 474 of an absorbent member 476, applicator 479 has a cover or shield 472 functioning similarly to cover 458 of FIG. 9. However, cover 472 is configured with a pair of rectilinear flanks 478 and a bottom portion 480 that extends parallel to a flat, distal end of attachment member 452. The bottom portion of cover 472 allows the frangible region 19 to pass therethrough forming an outlet port (see FIG. 10B) which in turn allows fluid held in source body 10 to pass through the outlet port, through the frangible region 19, and to escape from the aperture formed upon the breaking of frangible juncture 19.

The applicator 479 is formed by inserting cover 472 into and sealing it to the interior of absorbent member 476. The bottom portion 480 lies preferably flush with the proximal end of the absorbent member and is sealingly attached to frangible region 19.

Figure 11A:
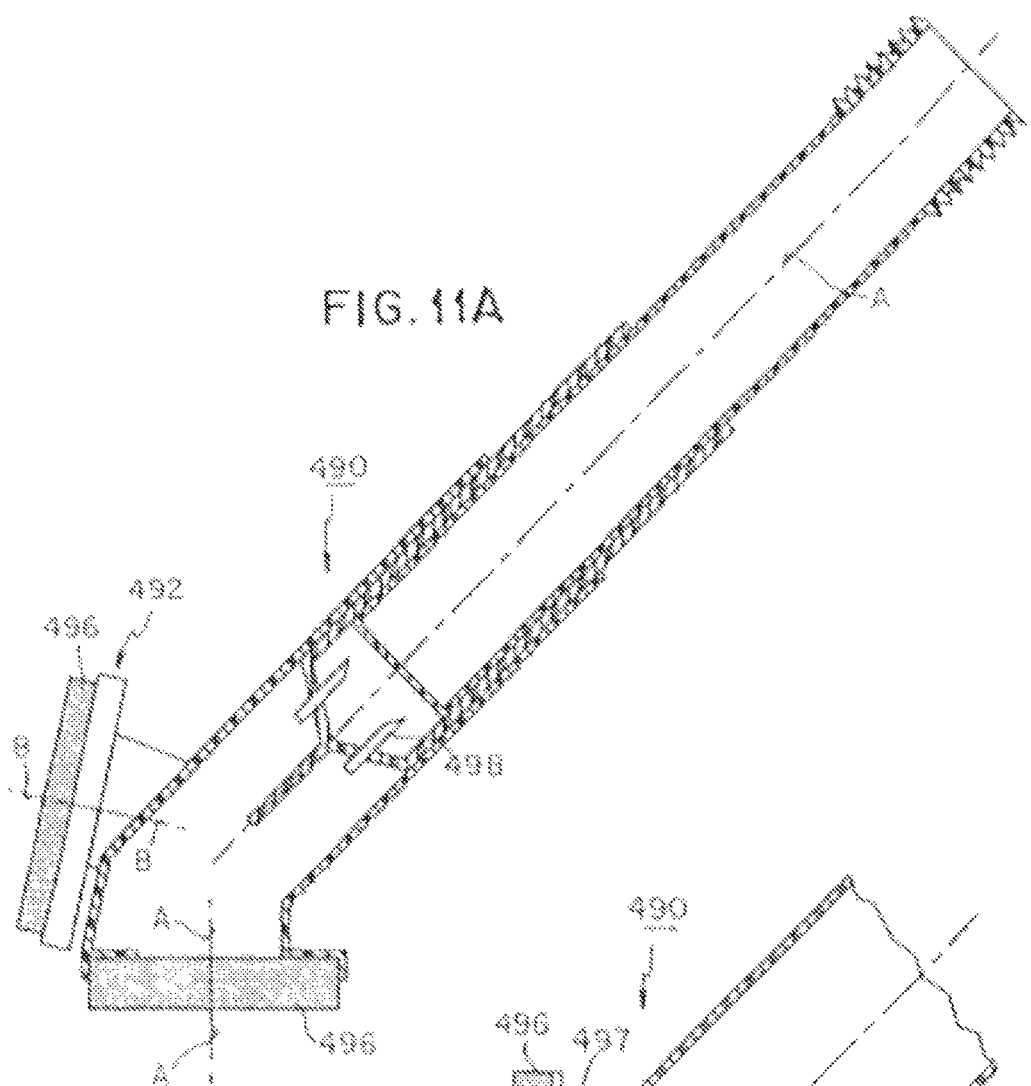
FIG. 11A is a side cross-sectional view of a dispensing applicator according to the present invention.
Figure 11B:
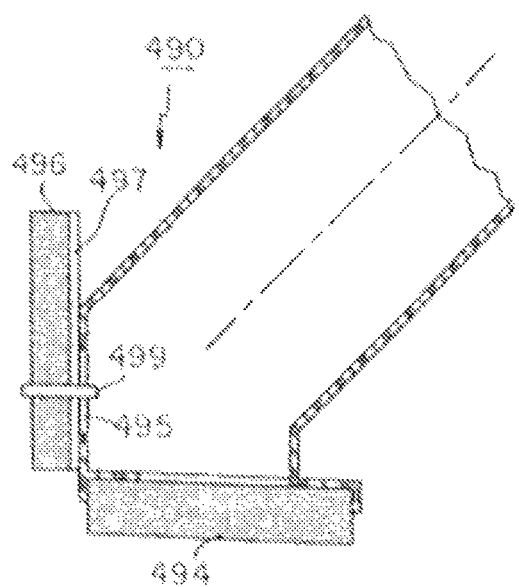
FIG. 11B is a side cross-sectional view of a further aspect of an embodiment of the dispensing applicator according to the present invention.

Embodiments of a dispensing applicator 490 illustrated in FIGS. 11A and 11b are conceptually close to the embodiment illustrated in FIGS. 5A and 5B and include an applicator head 492 which is formed with an absorbent member 494 and a swab member 496. The absorbent and swab members have a center axes A-A and B-B, respectively, which intersect one another forming an angle of about 80-100°.

The difference between the embodiment of FIGS. 5A and 5B and the current one includes utilization of one or more capillary vessels 498 provided instead of the frangible region. While, swab member 496 of FIG. 11A is prevented from fluid communication an interior of a fluid source body, swab member 496 of FIG. 11B is traversed by a capillary tube 499 and has an inner surface 497 in fluid communication with the interior via an opening 495, for the reasons explained above in reference to FIGS. 5A and 5B.

The present invention is primarily directed to a dispensing applicator for the application of liquids to the surface of the head, limbs, and/or body for medical purposes (i.e., pre-surgical disinfection). However, dispensing applicators according to the present invention may be used in a wide variety of purposes and environments. For example, a dispensing applicator according to the present invention can be used for application of lubricant(s) or adhesive(s). The range of sizes can also vary widely, as long as the several wall thicknesses are controlled appropriately to afford the desired functional characteristics discussed herein. It should also be appreciated by those of skill in the art that the fluid reservoirs, in selected embodiments, are flexibly bounded and allow an operator to control volumetric application based on the amount of pressure applied to the exterior of the reservoir. As a consequence of this design, it should also be recognized by those of skill in the art, that an operator releasing a compressed reservoirs, may partially suction released fluid back into the reservoir and minimize pooling.

It will be understood that the present invention may be embodied in other specific forms without departing from the spirit or central characteristics thereof. The present examples and embodiments, therefore, are to be considered in all respects as illustrative and not restrictive, and the invention is not to be limited to the details given herein.

Having described at least one of the preferred embodiments of the present invention with reference to the accompanying drawings, it is to be understood that such embodiments are merely exemplary and that the invention is not limited to those precise embodiments, and that various changes, modifications, and adaptations may be effected therein by one skilled in the art without departing from the scope or spirit of the invention as defined in the appended claims. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. A liquid dispensing applicator, comprising:
a liquid source for housing a liquid, the liquid source having a first end and a second end, the second end being closed;
an absorbent member including a swab member for dispensing said liquid, the swab member being irremovably disposed at the first end;
at least one capillary member including a capillary tube that traverses the absorbent member and that is in fluid communication with the liquid source, the capillary tube directing fluid out from the liquid source onto an exterior of the swab member upon application of pressure to the liquid source, the capillary tube permitting flow of fluid from the liquid source to the swab member only upon application of a predetermined amount of pressure to an exterior of the liquid source;
an attachment member coupled to the first end of the liquid source to secure the absorbent member to the liquid source, the attachment member having a through passage fluidically connecting the liquid source and the absorbent member; and
an applicator tip extending outwardly from the attachment member into the absorbent member, the applicator tip being disposed at a distal end of the attachment member and comprising a frangible portion and a tongue member.

2. The liquid dispensing applicator of claim 1, wherein:
the swab member includes an inner surface in fluid communication with the liquid source.

3. The liquid dispensing applicator of claim 2, wherein:
the absorbent member is not in fluid communication with the liquid source.

4. The liquid dispensing applicator of claim 1, further comprising:
an absorbent member, the absorbent member being adjacent to the swab member.

5. The liquid dispensing applicator of claim 4, wherein:
the liquid source has an axis extending lengthwise through the liquid source, the axis extending lengthwise through the liquid source being disposed substantially between the swab and absorbent members.

6. The liquid dispensing applicator of claim 1, wherein:
the absorbent member and the swab member have center axes extending through exterior surfaces thereof, the center axes being orthogonal with respect to one another.

7. The liquid dispensing applicator of claim 1, wherein:
the attachment member is configured to direct liquid from the liquid source toward a center axis extending lengthwise through the liquid source.

8. A liquid dispensing applicator, comprising:
a liquid source for housing a liquid, the liquid source having a first end and a second end, the second end being closed;
an absorbent member being disposed at the first end of the liquid source;
an attachment member for insertion into the first end of the liquid source to secure the absorbent member to the liquid source, the attachment member having a through passage fluidically connecting the liquid source and the absorbent member;
an applicator tip fluidically connected to the liquid source, the applicator tip including a frangible juncture and a tongue member coupled to the frangible juncture, application of force to the tongue member causing the frangible juncture to fracture while remaining attached to the tongue member, resulting in at least one aperture to form through which liquid from the liquid source is dischargeable, the applicator tip extending outwardly from the attachment member into the absorbent member; and
at least one capillary member including a capillary tube that traverses the absorbent member and that is in fluid communication with the liquid source, the capillary tube directing fluid out from the liquid source onto an exterior of the absorbent member upon application of pressure to the liquid source, the capillary tube permitting flow of fluid from the liquid source to the absorbent member only upon application of a predetermined amount of pressure to an exterior of the liquid source.

9. The liquid dispensing applicator of claim 8, wherein:
the tongue member further comprises:
at least one reinforcing rib connected proximate to frangible juncture.

10. The liquid dispersing applicator of claim 9, wherein:
the at least one reinforcing rib is configured to inhibit flexing of the tongue member and to concentrate the applied force at the frangible juncture.

11. The liquid dispersing applicator of claim 9, wherein:
the at least one reinforcing rib includes a first rib proximate a first end of the frangible juncture and a second rib proximate a second end of the frangible juncture and a third rib therebetween, the first and second ribs being configured to concentrate an applied force and break proximate said respective frangible junctures while the third rib remains secured to the frangible juncture.

12. The liquid dispersing applicator of claim 8, wherein:
the tongue member is hingedly connected to the frangible juncture, flexing of the tongue member relative to the frangible juncture causing the frangible juncture to fracture.

13. The liquid dispersing applicator of claim 12, wherein:
the absorbent applicator member is multi-sided.

14. The liquid dispersing applicator of claim 8, wherein:
the applicator tip is disposed within an absorbent applicator member.

* * * * *